United States Patent
Kawase (10) Patent No.: US 10,607,722 B2
(45) Date of Patent: Mar. 31, 2020

(54) DATA-PROCESSING FOR CHROMATOGRAPHIC MASS SPECTROMETRY

(71) Applicant: SHIMADZU CORPORATION, Kyoto-shi, Kyoto (JP)

(72) Inventor: Tomohiro Kawase, Kyoto (JP)

(73) Assignee: Shimadzu Co., Kyoto (JP)

( * ) Notice: Subject to any disclaimer, the term of this patent is extended or adjusted under 35 U.S.C. 154(b) by 1211 days.

(21) Appl. No.: 13/874,156

(22) Filed: Apr. 30, 2013

(65) Prior Publication Data

US 2013/0297230 A1 Nov. 7, 2013

(30) Foreign Application Priority Data

May 7, 2012 (JP) .................................. 2012-105687

(51) Int. Cl.
*G01N 31/00* (2006.01)
*G16C 20/20* (2019.01)
(Continued)

(52) U.S. Cl.
CPC ......... *G16C 20/20* (2019.02); *G01N 30/8662* (2013.01); *H01J 49/0036* (2013.01)

(58) Field of Classification Search
CPC . G06F 19/703; G01N 30/8662; H01J 49/0036
(Continued)

(56) References Cited

U.S. PATENT DOCUMENTS 6,989,100 B2 * 1/2006 Norton ............... G01N 30/8624
210/198.2

7,653,496 B2 * 1/2010 Li ........................ G01N 27/62
702/2
2005/0258355 A1 * 11/2005 Ogata ................ G01N 30/8675
250/281
(Continued)

FOREIGN PATENT DOCUMENTS

JP 2001-165922 A 6/2001
JP 2011-237311 A 11/2011
(Continued)

OTHER PUBLICATIONS

Examination Report Received for Japanese Patent Application No. 2012-105687, dated Apr. 14, 2015, 5 pages (2 pages of English Translation and 3 pages of Official Copy).
(Continued)

*Primary Examiner* — Michael P Nghiem
(74) *Attorney, Agent, or Firm* — Chris Mizumoto (57) ABSTRACT

Provided is a system for helping an operator determine the target ion, collision energy and other analysis conditions. A chromatogram selected by an operator is displayed in a chromatogram display area of an MRM measurement parameter determination window. When the operator selects a point on this chromatogram, the name of a target compound which is registered in an event linked with a range of time including the selected point in time is displayed on a compound name display area. A plurality of mass spectra collected at that point in time are also displayed in a mass spectra display area in a vertically arranged form, using the same scale on the mass axis and the same scale on the intensity axis, with the scales of their mass axes aligned with each other in the vertical direction. The operator can then check whether the selected peak corresponds to the target compound.

11 Claims, 3 Drawing Sheets

(51) Int. Cl.
*G01N 30/86* (2006.01)
*H01J 49/00* (2006.01)

(58) Field of Classification Search
USPC .......................................................... 702/32
See application file for complete search history.

(56) References Cited

U.S. PATENT DOCUMENTS

| 2013/0289893 | A1* | 10/2013 | Kawase | H01J 49/0036 |
| | | | | 702/23 |
| 2014/0012515 | A1* | 1/2014 | Taneda | G06F 19/708 |
| | | | | 702/32 |
| 2014/0014833 | A1* | 1/2014 | Sekiya | G01N 30/8651 |
| | | | | 250/288 |
| 2014/0132607 | A1* | 5/2014 | Kawana | G01N 30/8675 |
| | | | | 345/440 |
| 2015/0247829 | A1* | 9/2015 | Sumiyoshi | G01N 30/8651 |
| | | | | 250/288 |
| 2016/0033457 | A1* | 2/2016 | Mishima | G01N 30/86 |
| | | | | 702/25 |
| 2016/0231297 | A1* | 8/2016 | Noda | G01N 30/74 |
| 2017/0138916 | A1* | 5/2017 | Sumiyoshi | G01N 30/7233 |

FOREIGN PATENT DOCUMENTS

| JP | 2011-242255 A | 12/2011 |
| JP | 2011-249109 | 12/2011 |

OTHER PUBLICATIONS

Examination report received for 201310165158.X dated Jun. 17, 2014, 8 pages (2 pages of English Translation and 6 pages of Official Copy).

\* cited by examiner

DATA-PROCESSING FOR CHROMATOGRAPHIC MASS SPECTROMETRY

TECHNICAL FIELD

The present invention relates to a system for processing data collected by a chromatograph mass spectrometer including a chromatograph, such as a gas chromatograph (GC) or liquid chromatograph (LC), combined with a mass spectrometer, and for displaying a measured result on a display screen.

BACKGROUND ART

A method called an MS/MS analysis (or tandem analysis) is widely used as one of the mass spectrometric techniques for identification, structural analyses or quantitative determination of compounds having large molecular weights. There are various kinds of mass spectrometers with different configurations designed for the MS/MS analysis, among which tandem quadrupole mass spectrometers are characterized by their relatively simple structure as well as easy operation and handling.

In a generally used tandem quadrupole mass spectrometer, ions generated from a sample in an ion source are introduced into a first quadrupole mass filter (which is often represented as "Q1"), in which an ion having a specific mass-to-charge ratio (m/z) is selected as a precursor ion. This precursor ion is introduced into a collision cell containing an ion guide with four or more poles (this ion guide is commonly represented as "q2"). A collision-induced dissociation (CID) gas, such as argon, is supplied to this collision cell, and the precursor ion in the collision cell collides with this CID gas, to be fragmented into various kinds of product ions. These product ions are introduced into a second quadrupole mass filter (which is often represented as "Q3"), which selectively allows a product ion having a specific mass-to-charge ratio (m/z) to pass through it and reach a detector, to be thereby detected.

The tandem quadrupole mass spectrometer can be used independently. However, this device is often coupled with a chromatograph, such as a gas chromatograph (GC) or liquid chromatograph (LC). In recent years, chromatograph tandem quadrupole mass spectrometers have become vital devices in the field of analyzing a trace amount of a sample containing a large amount of compounds or a sample contaminated with various impurities, such as testing residual pesticides in foodstuffs, testing environmental pollutants, checking the concentration of medicinal chemicals in blood, or screening drugs or poisonous substances.

MS/MS analyses by chromatograph tandem quadrupole mass spectrometers can be conducted in various measurement modes, such as a multiple reaction monitoring (MRM) mode, precursor-ion scan mode, product-ion scan mode, and neutral-loss scan mode (see Patent Document 1). In the MRM mode, the mass-to-charge ratio at which ions are allowed to pass through is fixed in each of the first and second quadrupole mass filters so as to fragment a specific kind of precursor ion and measure an intensity (or amount) of a specific kind of product ion resulting from the fragmentation. The two-stage mass filtering in the MRM measurement eliminates unwanted components other than those to be analyzed, ions originating from impurities, and neutral particles, so that an ion intensity signal with high signal-to-noise ratio can be obtained. Due to this feature, the MRM measurement is particularly effective for the quantitative analysis of a trace amount of a component. For example, gas chromatograph tandem mass spectrometers (GC/MS/MS) are frequently operated in the MRM mode to perform a simultaneous multi-component quantitative analysis of residual pesticides, which requires determining the quantity of an extremely small amount of components.

To ensure a high accuracy of quantitative determination by the MRM measurement, it is necessary to set appropriate MRM measurement parameters for each compound, such as the mass-to-charge ratio of a precursor ion, the mass-to-charge ratio of a product ion and the collision energy. In the case of quantitative analyses, a mass-to-charge ratio corresponding to the maximal intensity of the ions originating from the compound in question is selected as the aforementioned mass-to-charge ratio. An ion having the thus selected mass-to-charge ratio is called the target ion. If there is a foreign component which has a peak at the same mass-to-charge ratio as that of the target ion on a mass spectrum and which has roughly the same retention time as the target ion, it is difficult to distinguish the target compound from the foreign component by only the target ion. In one commonly used solution to this problem, an ion which originates from the target compound but has a different mass-to-charge ratio is designated beforehand as a qualifier ion, and the relative ratio of the peak intensity corresponding to the qualifier ion to the peak intensity corresponding to the target ion on a mass spectrum representative of the peak located on the mass chromatogram of the target ion is calculated. If this ratio ("qualifier ion ratio") is within a predetermined range, the peaks on the mass chromatogram can be considered to have originated from the target compound.

To determine the optimal target ion, qualifier ion or collision energy for each compound, an MS/MS analysis using a chromatograph tandem quadrupole mass spectrometer is performed on a sample containing a target compound a plurality of times while varying the collision energy. Then, a plurality of mass spectra (product-ion spectra) corresponding to different collision energies obtained in the vicinity of the retention time at which the target compound should appear are compared to determine an optimal target ion, qualifier ion, collision energy, and so on. Such a series of operations and determinations are performed by an analysis operator.

That is to say, in a conventional data-processing system for chromatographic tandem quadrupole mass spectrometry, after measurement data by an MS/MS analysis are collected, when the operator selects a set of measurement data that should be re-analyzed, the selected data are read from a storage, and a total ion chromatogram is created from those data and shown on a display screen. On this total ion chromatogram, the operator selects a peak or point that seems to correspond to the target compound, by means of a pointing device or other kinds of input devices. Then, a mass spectrum actually measured at the point in time corresponding to the selected point is created and shown in a different area on the display screen. Subsequently, when the operator similarly selects another set of measurement data obtained under a different amount of collision energy, the selected data are read from the storage, and another mass spectrum is created from the data and shown on the same display screen. Thus, a plurality of mass spectra obtained under different amounts of collision energy can be simultaneously shown on the same display screen. By comparing the displayed mass spectra, the operator can select an appropriate target ion and qualifier ion as well as appropriate collision energy.

If the sample contains only the target compound, the previously described process causes no problem. Actually, samples used for such purposes normally contain a plurality of compounds so as to allow parallel determination of the measurement parameters for multiple compounds. Therefore, operators need to check whether or not a peak located on the total ion chromatogram corresponds to an intended target compound. For that purpose, it is necessary to refer to another type of information, such as a compound table. In the case of simultaneous multiple-component quantitative determination, the aforementioned checking is required for each of a large number of compounds. This work is cumbersome and lowers the working efficiency.

The previously described problem occurs not only in the determination of MRM measurement parameters used in a chromatograph tandem quadrupole mass spectrometer, but also in other situations, such as the determination of the voltage settings of an ion transport optical system used in a chromatograph quadrupole mass spectrometer.

BACKGROUND ART DOCUMENT

Patent Document

Patent Document 1: JP-A 2011-249109

SUMMARY OF THE INVENTION

Problem to be Solved by the Invention

The present invention has been developed to solve the aforementioned problem. Its primary objective is to provide a system for facilitating the determination of measurement parameters (e.g. the target ion, qualifier ion and collision energy for each compound in a chromatograph tandem quadrupole mass spectrometer) so as to reduce the workload on an operator due to the visual checking and improve the working efficiency while decreasing mistakes in the work process.

Means for Solving the Problems

The present invention aimed at solving the previously described problem is a data-processing system for chromatographic mass spectrometry for processing chromatographic mass spectrometry data repeatedly collected by a chromatograph mass spectrometer with the elapse of time and for showing a measured result on a screen of a display unit, including:

a) a compound information memory for storing compound names, each name being associated with a retention time or a period of time including the retention time, or associated with both the period of time and an analysis condition of a mass spectrometry to be performed within that period of time;

b) a first display processor for displaying, on a portion of the screen of the display unit, a chromatogram created from the chromatographic mass spectrometry data;

c) a selector for allowing an operator to select a temporal location on the chromatogram displayed on the screen of the display unit by the first display processor; and d) a second display processor for searching the compound information memory for a compound name associated with a retention time or a period of time corresponding to the temporal location selected on the chromatogram, or associated with both the period of time and the analysis condition of the mass spectrometry under which the chromatographic mass spectrometry data for creating the chromatogram within the period of time is acquired, and for showing the compound name and a mass spectrum on the screen together with the chromatogram, the mass spectrum being based on either the chromatographic mass spectrometry data acquired at the selected temporal location or the chromatographic mass spectrometry data used for creating the chromatogram at the selected temporal location and acquired at the selected temporal location.

In the data-processing system for chromatographic mass spectrometry according to the present invention, under the condition that chromatographic mass spectrometry data for a target sample have been collected by a chromatograph mass spectrometer, when an operator enters a predetermined command, the first display processor creates a chromatogram based on the collected chromatographic mass spectrometry data and shows it on a portion of the screen of the display unit. In the case where the mass spectrometer is a quadrupole mass spectrometer having a single quadrupole mass filter, the chromatographic mass spectrometry data are obtained, for example, by repeating a scan measurement over a predetermined range of mass-to-charge ratios in the mass spectrometer, or by repeating a selected ion monitoring (SIM) measurement for a plurality of predetermined mass-to-charge ratios in the mass spectrometer. In the case where the mass spectrometer is a tandem quadrupole mass spectrometer having two tandemly arranged quadrupole mass filters, the chromatographic mass spectrometry data are obtained, for example, by repeating a product-ion scan measurement over a predetermined range of mass-to-charge ratios in the mass spectrometer, or by repeating an MRM measurement for a plurality of predetermined mass-to-charge ratios in the mass spectrometer. In any of these cases, the chromatogram may be either a total ion chromatogram obtained by summing the ion intensities at each point of measurement time or a mass chromatogram obtained at a specific mass-to-charge ratio.

On the chromatogram shown on the display screen, the operator selects a temporal location (e.g., a point in time or range of time) through the selector. For example, when a mass spectrum characteristic of the target compound needs to be observed, the operator normally guesses which peak on the chromatogram corresponds to the target compound and selects a point at or near the temporal location of the maximal intensity of the peak. In response to this selection, the second display processor accesses the compound information memory to obtain a compound name associated with the retention time or the period of time corresponding to the selected temporal location, or associated with both the period of time and the analysis condition of the mass spectrometry under which the chromatographic mass spectrometry data for creating the chromatogram within that period of time is acquired. Simultaneously, the second display processor obtains either the chromatographic mass spectrometry data acquired at the selected temporal location or the chromatographic mass spectrometry data used for creating the chromatogram at the selected temporal location and acquired at the selected temporal location, and creates a mass spectrum based on the obtained data. Then, it displays the compound name and the mass spectrum together with, and apart from, the chromatogram on the screen. The compound name may be superimposed on the display frame of the chromatogram.

Thus, the compound name corresponding to the peak selected on the chromatogram by the operator is immediately shown on the screen. The operator can easily and assuredly determine whether or not the selected peak corresponds to the correct compound for which the target ion and qualifier ion need to be chosen.

In the data-processing system for chromatographic mass spectrometry according to the present invention, one example of the "analysis condition of a mass spectrometry" is the "event number" in one embodiment of the present invention which will be described later.

In one preferable mode of the data-processing system for chromatographic mass spectrometry according to the present invention, when one set of chromatographic mass spectrometry data has been obtained for each of a plurality of measurements, the second display processor displays a plurality of mass spectra respectively based on a plurality of sets of chromatographic mass spectrometry data obtained at the selected temporal location, the mass spectra having the same scale on the mass axis and the same scale on the intensity axis and being vertically arranged on the screen together with the chromatogram.

One example of the chromatographic mass spectrometry data obtained for each of a plurality of measurements is chromatographic mass spectrometry data obtained for the same compound in the same sample under various measurement conditions differing in collision energy and/or other parameters in the previously described manner. In the previously described mode, a plurality of mass spectra created from a plurality of chromatographic mass spectrometry data obtained at the same temporal location are vertically arranged, using the same scale on the mass axis and the same scale on the intensity axis, so that operators can visually and intuitively compare the intensities of the peaks at the same mass-to-charge ratio on the displayed mass spectra.

In another preferable mode of the present invention, the second display processor interlocks a resizing operation of the mass axes and/or the intensity axes of the vertically arranged mass spectra. That is to say, when an operator performs an operation for resizing the mass axis and/or the intensity axis of one of the displayed mass spectra, the corresponding axes of the other mass spectra will also be automatically resited in the same way. Such an interlocked resizing allows operators to consistently compare the peak intensities at the same mass-to-charge ratio on the plurality of mass spectra, in whatever way the resiting is performed. This is effective for preventing an incorrect determination by the operator due to an erroneous operation or misunderstanding of the data.

Effect of the Invention

With the data-processing system for chromatographic mass spectrometry according to the present invention, the name of a compound having a retention time at any temporal location on a chromatogram can be checked by a very simple operation. Therefore, for example, when it is necessary to select a peak on a chromatogram and check actually measured mass spectra corresponding to that peak to determine a target ion, qualifier ion, collision energy or other measurement parameters for each compound in a chromatograph tandem quadruple mass spectrometer, the operator can easily check that the peak on the chromatogram is a peak which correctly corresponds to the target compound, whereby the working efficiency is improved and the number of incorrect operations is decreased.

BEST MODE FOR CARRYING OUT THE INVENTION

One embodiment of a gas chromatograph tandem quadrupole mass spectrometer (GC/MS/MS) having a data-processing system for chromatographic mass spectrometry according to the present invention is hereinafter described in detail with reference to the attached drawings.

Figure 1:
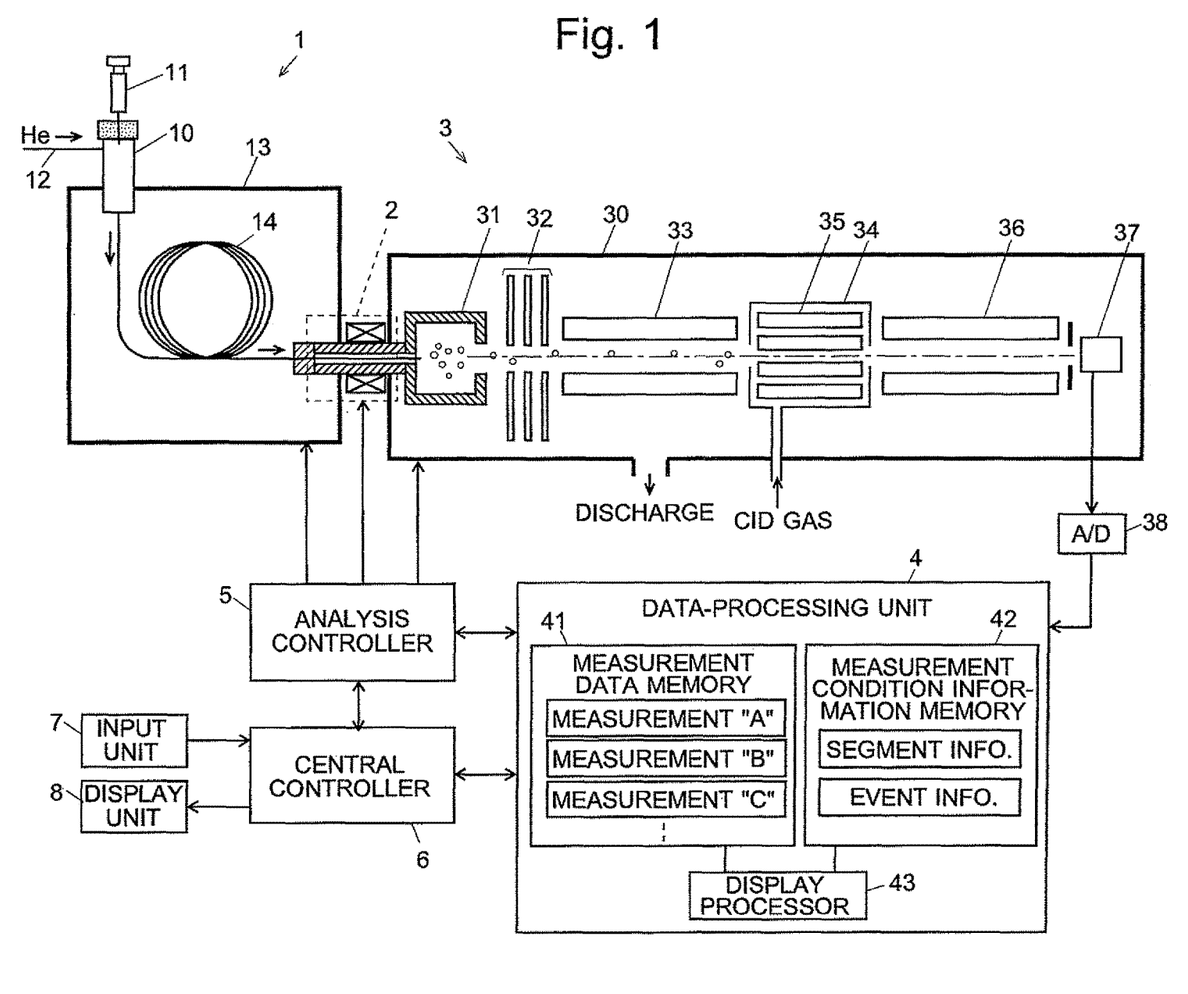
FIG. 1 is a schematic configuration diagram of one embodiment of a GC/MS/MS having a data-processing system for chromatographic mass spectrometry according to the present invention.

FIG. 1 is a schematic configuration diagram of the GC/MS/MS according to the present embodiment. In a gas chromatograph (GC) unit 1, a sample vaporization chamber 10 is provided at the inlet of a column 14, which is heated to an appropriate temperature by a column oven 13. A carrier gas 12 is supplied through a carrier-gas passage 12 to the sample vaporization chamber 10 at a predetermined flow rate and introduced into the column 14. In this state, when a trace amount of liquid sample is injected from a micro syringe 11 into the sample vaporization chamber 10, the liquid sample instantly vaporizes and is carried into the column 14 by the carrier-gas flow. While passing through the column 14, the sample gas is temporally separated into various compounds before arriving at the outlet of the column 14. After exiting the column 14, these compounds pass through the interface unit 2 including a heater and other elements, to be introduced into an ionization chamber 31 provided in a vacuum chamber 30 in a mass spectrometer (MS) unit 3.

The molecules of the compounds introduced into the ionization chamber 31 are ionized by an appropriate method, such as electron ionization (EI) or chemical ionization (CI). The produced ions are drawn to the outside of the ionization chamber 31 and converged by an ion lens 32, to be introduced into a space extending along the axis of a first quadrupole mass filter (Q1) 33, which consists of four rod electrodes. A voltage produced by superposing a DC voltage on an AC voltage is applied from a power source (not shown) to the first quadrupole mass filter 33, where only a specific kind of ion whose mass-to-charge ratio corresponds to the applied voltage is allowed to pass through the first quadrupole mass filter 33 in the axial direction thereof, to be introduced into a collision cell 34.

The collision cell 34 contains a multipole ion guide (q2) 35 for converging ions by the effect of a radio-frequency electric field. A collision-induced dissociation (CID) gas, such as argon gas, is continuously or intermittently introduced from the outside into the collision cell 34. The ions introduced into the collision cell 34 come in contact with the CID gas, to be fragmented into product ions. While being converged, the resultant fragment ions are introduced into a space extending along the axis of a second quadrupole mass filter (Q3) 36. Similar to the first quadrupole mass filter 33, the second quadrupole mass filter 36 consists of four rod electrodes. A voltage produced by superposing a DC voltage on an AC voltage is applied from a power source (not shown) to those rod electrodes. Only a specific kind of product ion whose mass-to-charge ratio corresponds to the applied voltage is allowed to pass through the second quadrupole mass filter 33 in the axial direction thereof and reach an ion detector 37.

The detection signal produced by the on detector 37 is converted into digital data by an analogue-to-digital (A/D) converter 38 and sent to a data-processing unit 4. The data-processing unit 4 includes a measurement data memory 41, a measurement condition information memory 42, a chromatogram creation processor 43 and other functional blocks to perform a process characteristic of the present invention. The operations of the GC unit 1, the interface unit 2 and the components included in the MS unit 3 are individually controlled by an analysis controller 5. A central controller 6, to which an input unit 7 (including a keyboard and a mouse or similar pointing device) and a display unit 8 are connected, is responsible for controlling input/output operations as well as basic system operations at higher levels than the analysis controller 5. The data-processing unit 4, the analysis controller 5 and the central controller 6 can be embodied by using a personal computer as the hardware resource and executing a preinstalled, dedicated controlling-and-processing software program on that personal computer.

The MS unit 3 of this GC/MS/MS can perform various modes of measurements. For example, the MRM mode, the precursor-ion scan mode, the product-ion scan mode or the neutral-loss scan mode can be used as a measurement mode for an MS/MS analysis, which involves a CID operation performed in the collision cell 34. For an analysis with no CID operation performed in the collision cell 34, the Q1SIM mode, the Q3SIM mode, the Q1 scan mode and the Q3 scan mode are available.

Figure 3:
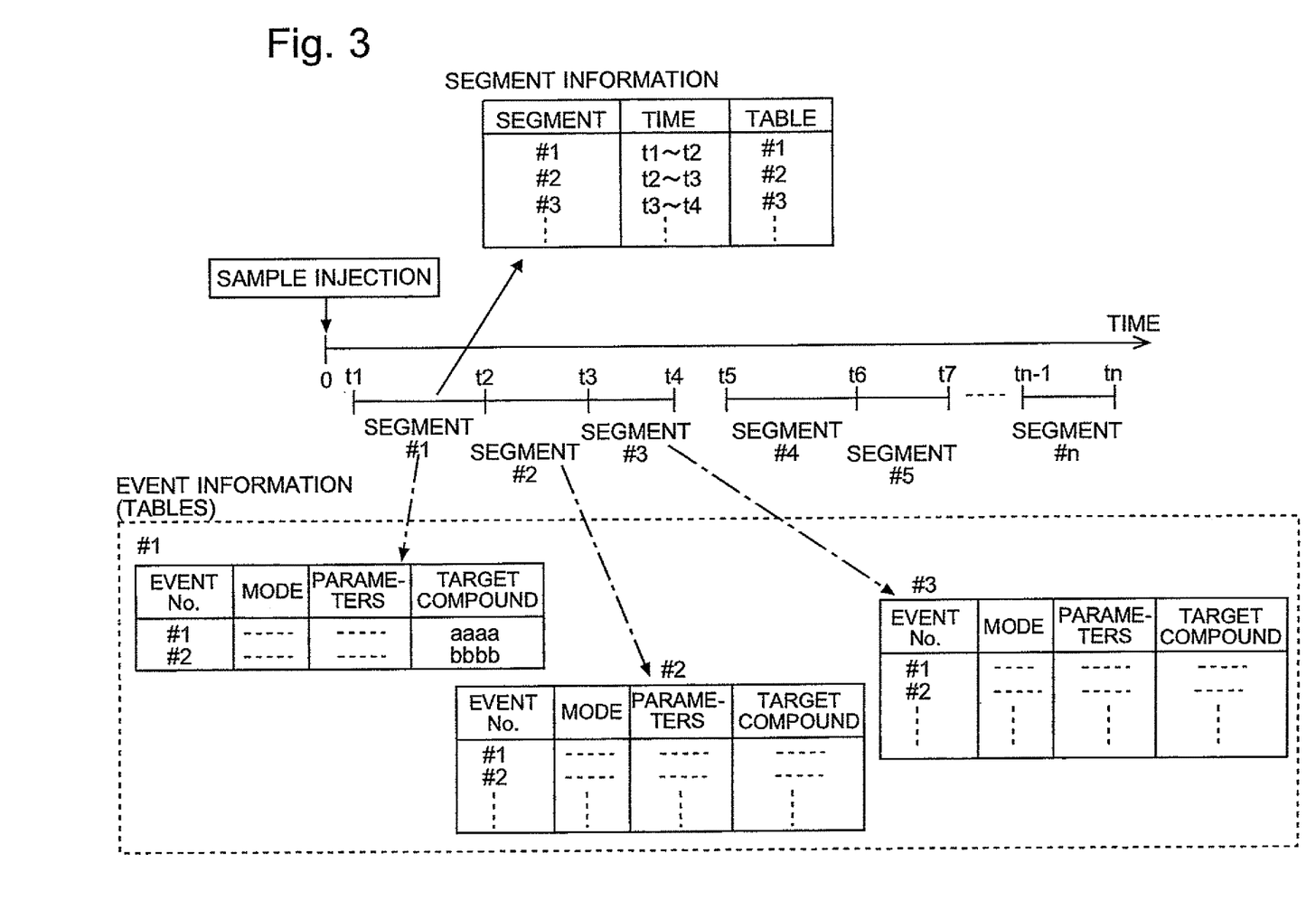
FIG. 3 is a conceptual diagram of segments and events specified for performing a measurement in the GC/MS/MS of the present embodiment.

In the GC/MS/MS of the present embodiment, the mode and conditions of the measurement can be specified in a manner to be described later so that the measurement can be performed while appropriately switching the aforementioned various measurement modes or the same mode of measurement can be performed while appropriately changing the measurement conditions (measurement parameters). FIG. 3 is a conceptual diagram of segments and events specified with respect to the elapse of time.

As shown in FIG. 3, the range of time from the beginning (sample injection) to the end of the analysis is divided into units of time called "segments", which can be freely set by operators. The segments can be set either continuously or discontinuously as long as they do not overlap each other. The information linking each segment with the corresponding range of time is aggregated as segment information data. The range of time (the beginning and ending points in time) of each segment can be arbitrarily set by users. However, in the case of a quantitative analysis using an MRM or SIM measurement, it is preferable to specify the range of time of each segment so that one segment is assigned to each of the target compounds separately located on a mass chromatogram.

Each measurement mode to be performed and the measurement conditions for that measurement mode (e.g. for the MRM mode, the conditions include the ink value to be selected by the first quadrupole mass filter 33 and the ink value to be selected by the second quadrupole mass filter 36) are specified as an "event." One or more events can be set for each segment. In addition to the measurement mode (e.g. the MRM mode) and the measurement conditions (parameter values) necessary for carrying out that measurement mode, other kinds of information, including the name of a compound to be analyzed by that event, can also be set for each segment. In the example shown in FIG. 3, a set of event information as described in table #1 is set for segment #1 covering the range of time from t1 to t2. More specifically, two events #1 and #2 as described in table #1 are set for segment #1. In segment #1, the name of the compound specified as the measurement target in event #1 is "aaaa", while the compound name specified in event #2 is "bbbb." Naturally, both "aaaa" and "bbbb" should be compounds which have known retention times (or retention indices) and are expected to exit from the column 14 within the range of time from t1 to t2 as defined by segment #1 and produce a peak or peaks on a chromatogram within that range of time. Thus, in the example of FIG. 3, two analyses according to the conditions respectively specified as events #1 and #2 in table #1 are cyclically (or alternately) repeated within the range of time from t1 to t2 to collect quantitative information for each of the two compounds "aaaa" and "bbbb."

A displaying process characteristic of the present invention is hereinafter described, taking an example of determining optimal parameters of an MRM measurement for a certain compound by the GC/MS/MS of the present embodiment.

To determine optimal parameters of an MRM measurement for a given compound, which specifically include the mass-to-charge ratio of a precursor ion, that of a product ion and collision energy, chromatographic mass spectrometry data are collected, for example, by performing a product-ion scan measurement for a sample containing the target compound for each level of collision energy while varying the collision energy in a stepwise manner, with the mass-to-charge ratio of the precursor-ion fixed at a predetermined value. For this measurement, the operator should previously set a segment taking into account the known retention time of the target compound, and specify an event so that a product-ion scan measurement will be performed during the period of time corresponding to that segment, using the measurement parameters in which the mass-to-charge ratio of the precursor ion is set at a predetermined value, the range of mass-to-charge ratios of the product ions is set at a predetermined range, and the aforementioned target compound is selected as the compound to be analyzed.

Consider the case where three sets of measurement data have been respectively obtained by three different measurements, labeled "A", "B" and "C", performed under different collision energies. These measurement data are individually stored as data files in the measurement data memory 41. The information relating to the segments and events specified in the previously described manner are stored in the measurement condition information memory 42.

Figure 2:
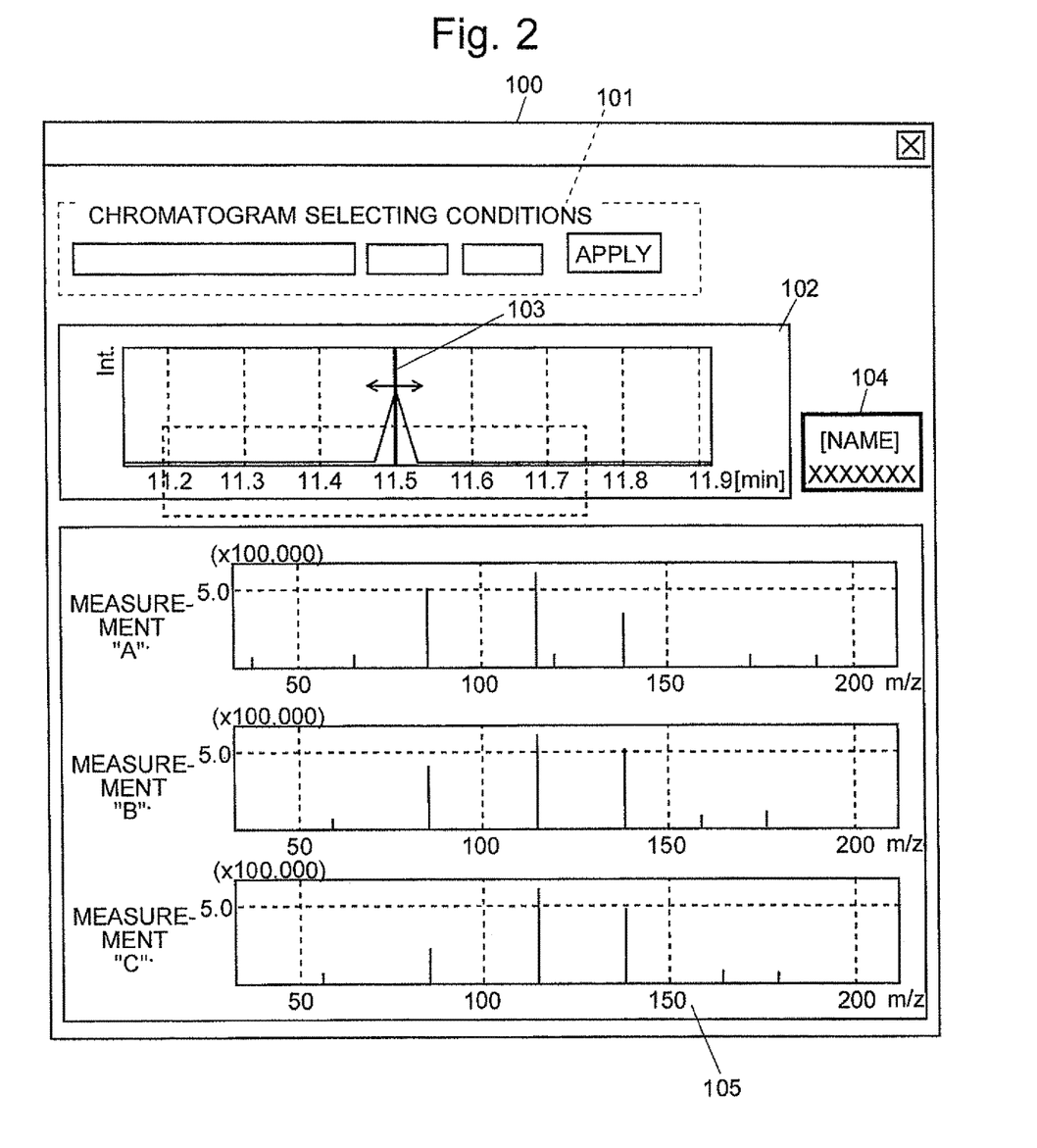
FIG. 2 is a diagram showing one example of the display screen shown in a process of determining MRM measurement parameters in the GC/MS/MS of the present embodiment.

When the operator performs a predetermined operation through the input unit 7 to determine optimal parameters of the MRM measurement for a given compound, the display processor 43 receives the input command via the central controller 6 and shows an MRM measurement parameter determination window 100, as shown in FIG. 2, on the screen of the display unit 8. The MRM measurement parameter determination window 100 includes a chromatogram selection input area 101 having buttons and text boxes for the operators to input the selection of a chromatogram to be displayed on a chromatogram display area 102. One of the buttons is used for selecting an event number. For example, if the operator selects event #1, a chromatogram is created from the data collected by the measurement specified in event #1 in each of the segments, and is shown on the chromatogram display area 102. The selection of the chromatogram to be displayed may also be achieved in a different way, e.g. by allowing the operator to select or specify the name of a data file containing the desired chromatographic mass spectrometry data. The type of the chromatogram to be displayed depends on the measurement mode; normally, it is either a total ion chromatogram or mass chromatogram. In the case where an SIM or MRM measurement has been performed for each of a plurality of mass-to-charge ratios, it is also possible to display a chromatogram obtained by summing only the ion intensities observed at those mass-to-charge ratios.

When an appropriate selection input is made in the chromatogram selection input area 101 by the operator, the display processor 43 reads out the selection input data from the measurement data memory 41, creates a chromatogram from the read data and draws it on the chromatogram display area 102. If the selection input is appropriately made so as to display a chromatogram based on the result of a measurement performed on a sample containing the target compound, a peak originating from that target compound should appear on the resultant chromatogram. Accordingly, the operator should appropriately adjust the displayed range of time axis so that a peak located at or near the retention time of the target compound will be included in the display frame.

With a chromatogram peak which is most likely to have originated from the target compound being displayed as shown in FIG. 2, the operator selects a desired point in time on the chromatogram by means of a pointing device. Upon this operation, the display processor 43 displays a chromatogram in the following manner: A marker 103 is shown at the selected point in time on the chromatogram. The segment which corresponds to the range of time including the selected point in time is identified. Then, with reference to the segment information and event information as shown in FIG. 3, a compound name corresponding to the event number which is associated with the identified segment and which is currently specified to display the chromatogram in the selected range of time is read out. The thus read compound name is shown in letters in the compound name display area 104 of the MRM measurement parameter determination window 100. Mass spectrum data obtained at the selected point in time according to the selected event are read from each of the data files stored in the measurement data memory 41, and a mass spectrum is created from each set of the read data. The created mass spectra are vertically arranged in the mass spectra display area 105 below the chromatogram display area 103, using the same scale on the mass axis (m/z axis) and the same scale on the intensity axis, with the scales of their mass axes aligned with each other in the vertical direction.

As just described, the present system displays, in the compound name display area 104, the compound name which is beforehand associated with the point in time selected on the chromatogram and the event relating to the chromatogram at that point in time. This information allows the operator to quickly determine whether or not the chromatogram peak currently selected for investigation correctly corresponds to the target compound. An incorrect compound name displayed on the screen strongly suggests that some mistake has occurred, such as the selection of a chromatogram peak that has originated from a different compound or an incorrect setting of the segments or events. In such a case, the operator can locate the cause of the problem by performing appropriate tasks or operations, such as searching the chromatogram for another peak.

In the example shown in FIG. 2, three mass spectra are vertically arranged in the mass spectra display area 105. In some cases, there are a larger number of mass spectra to be displayed. One method for dealing with such a situation is to reduce the vertical size of each mass spectrum so that all the mass spectra can be simultaneously viewed. Another method is to use a vertically scrollable display area so that the operator can browse through all the mass spectra without changing their vertical size.

If the operator moves the marker 103 along the time axis by a dragging or similar operation, the display processor 43 performs the previously described processes at the new position of the marker 103 on the time axis. As a result, the compound name displayed in the compound name display area 104 and the mass spectra displayed in the mass spectra display area 105 are appropriately updated.

The mass axes and the intensity axes of the mass spectra shown in the mass spectra display area 105 can be appropriately resized, for example, by selecting a size from a menu list or performing a dragging operation. When such an operation is performed on one mass spectrum, the display processor 43 applies the same resizing operation to the corresponding axes of the other mass spectra shown on the screen. Thus, the mass axes and the intensity axes of the plurality of mass spectra shown in the mass spectra display area 105 are maintained to be identical in scale. This allows the operator to intuitively check whether or not the peaks on the plurality of mass spectra obtained at the same point in time correspond to the same mass-to-charge ratio. It is also easy to compare peak intensities between different mass spectra.

By comparing a plurality of mass spectra in the previously described manner, the operator can determine the optimal amount of collision energy for the target compound. It is also possible to select the optimal target ion and qualifier ion based on the mass spectrum which has been obtained under that collision energy.

In some cases, two or more compounds are contained in one sample and the MRM measurement parameters need to be determined for each of those compounds. In such cases, a chromatogram peak corresponding to the next compound can be displayed by setting a new event number and appropriately adjusting the time axis of the chromatogram, after which the previously described operations and processes can be repeated.

It should be noted that the previously described embodiment is a mere example, and any change, modification or addition appropriately made within the spirit of the present invention will evidently fall within the scope of claims of the present patent application.

For example, unlike the previous embodiment in which the name of a target component is registered as one item of an event specified for a segment covering a specific range of time, it is possible to use a list or table for allowing the name of a target component to be registered as one item of an event which is directly linked with a specific retention time or a range of time including that retention time. It is also possible to integrate the segment with the event to create an extended version of the event in which the range of time to execute that event, the measurement mode, the measurement conditions, the name of the target compound and other kinds of information can be registered as event information.

Although the previously described embodiment was an example of applying the data-processing system for chromatographic mass spectrometry according to the present invention to a GC/MS/MS, it is evident that the present invention can also be applied to LC/MS/MS as well as GC/MS/MS. It is also evident that the MS unit 3, which is a tandem quadrupole mass spectrometer in the previous embodiment, may be a quadrupole mass spectrometer having a single quadrupole mass filter.

EXPLANATION OF NUMERALS

1 . . . Gas Chromatograph (GC) Unit
10 . . . Sample Vaporization Chamber 11 ... Micro Syringe
12 ... Carrier-Gas Passage
13 ... Column Oven
14 ... Column
2 ... Interface Unit
3 ... Mass Spectrometer (MS) Unit
30 ... Vacuum Chamber
31 ... Ionization Chamber
32 ... Ion Lens
33 ... First Quadrupole Mass Filter
34 ... Collision Cell
35 ... Multi-Pole on Guide
36 ... Second Quadrupole Mass Filter
37 ... Ion Detector
38 ... Analogue-to-Digital (A/D) Converter
4 ... Data-Processing Unit
41 ... Measurement Data Memory
42 ... Measurement Condition Information Memory
43 ... Display Processor
5 ... Analysis Controller
6 ... Central Controller
7 ... Input Unit
8 ... Display Unit
100 ... MRM Measurement Parameter Determination Window
101 ... Chromatogram Selection Input Area
102 ... Chromatogram Display Area
103 ... Marker
104 ... Compound Name Display Area
105 ... Mass Spectra Display Area

The invention claimed is:

1. A data-processing system for chromatographic mass spectrometry for processing chromatographic mass spectrometry data collected by a chromatograph mass spectrometer and for showing a measured result on a screen of a display unit, comprising:
   a) a compound information memory for storing names of compounds, each of the names being associated with a retention time or a period of time including the retention time, or associated with both the period of time and a mass analysis condition to be performed within that period of time, and each of the compounds being analyzed at the retention time or in the period of time including the retention time;
   b) a display processor for displaying, on a portion of the screen of the display unit, a chromatogram created from the chromatographic mass spectrometry data; and
   c) a selector for allowing an operator to select a temporal location on the chromatogram displayed on the screen of the display unit by the display processor;
   wherein the display processor:
      searches the compound information memory for a name of a compound associated with a retention time or a period of time including the retention time, corresponding to the temporal location selected through the selector on the chromatogram, and
      shows the compound name and a plurality of mass spectra on the screen together with the chromatogram, the plurality of mass spectra being based on the chromatographic mass spectrometry data acquired at the selected temporal location,
   whereby the operator is able to check whether or not a peak at the temporal location on the chromatogram corresponds to an intended target compound to improve working efficiency and decrease incorrect operations.

2. The data-processing system for chromatographic mass spectrometry according to claim 1, wherein: when one set of chromatographic mass spectrometry data has been obtained for each of a plurality of measurements, the display processor displays a plurality of mass spectra respectively based on a plurality of sets of chromatographic mass spectrometry data obtained at the selected temporal location, each of the mass spectra having a same scale on a mass axis and a same scale on an intensity axis as the other mass spectra and being vertically arranged on the screen together with the chromatogram.

3. The data-processing system for chromatographic mass spectrometry according to claim 2, wherein:
   the display processor interlocks a resizing operation of the mass axis and/or the intensity axis of each of the vertically arranged mass spectra.

4. The data-processing system for chromatographic mass spectrometry according to claim 1, wherein the display processor searches the compound information memory for a name of a compound also associated with the mass analysis condition under which the chromatographic mass spectrometry data for creating the chromatogram within the period of time is acquired.

5. The data-processing system for chromatographic mass spectrometry according to claim 1, wherein the plurality of mass spectra being further based on the chromatographic mass spectrometry data used for creating the chromatogram at the selected temporal location.

6. A data-processing system for chromatographic mass spectrometry for processing chromatographic mass spectrometry data collected by a chromatograph mass spectrometer and for showing a measured result on a screen of a display unit, comprising:
   a compound information memory for storing names of compounds, each of the names being associated with a retention time or a period of time including the retention time, or associated with both the period of time and a mass analysis condition to be performed within that period of time, and each of the compounds being analyzed at the retention time or in the period of time including the retention time;
   a display processor for displaying, on a portion of the screen of the display unit, a chromatogram created from the chromatographic mass spectrometry data; and
   a selector for allowing an operator to select a temporal location on the chromatogram displayed on the screen of the display unit by the display processor;
   wherein the display processor:
   searches the compound information memory to obtain a compound name associated with a retention time or a period of time including the retention time, corresponding to the temporal location selected through the selector;
   creates a plurality of mass spectra based on the chromatographic mass spectrometry data acquired under various measurement conditions for determining optimal measurement parameters of the compound at the selected temporal location; and
   displays the compound name and the mass spectrum together with, and apart from, the chromatogram on the screen, wherein the compound name may be superimposed on the display frame of the chromatogram,
   whereby the operator is able to check whether or not a peak at the temporal location on the chromatogram corresponds to an intended target compound to improve working efficiency and decrease incorrect operations.

7. The data-processing system for chromatographic mass spectrometry according to claim 6, wherein the display processor searches the compound information memory for a name of a compound also associated with the mass analysis condition under which the chromatographic mass spectrometry data for creating the chromatogram within the period of time is acquired.

8. The data-processing system for chromatographic mass spectrometry according to claim 6, wherein the plurality of mass spectra being further based on the chromatographic mass spectrometry data used for creating the chromatogram at the selected temporal location.

9. A data-processing system for chromatographic mass spectrometry for processing chromatographic mass spectrometry data collected by a chromatograph mass spectrometer and for showing a measured result on a screen of a display unit, comprising:
- a compound information memory for storing names of compounds, each of the names being associated with a retention time or a period of time including the retention time, or associated with both the period of time and a mass analysis condition to be performed within that period of time, and each of the compounds being analyzed at the retention time or in the period of time including the retention time;
- a display processor for displaying, on a portion of the screen of the display unit, a chromatogram created from the chromatographic mass spectrometry data; and
- a selector for allowing an operator to select a temporal location on the chromatogram displayed on the screen of the display unit by the display processor;
- wherein the display processor:
- displays a marker at the selected temporal location on the chromatogram;
- searches the compound information memory to obtain a compound name associated with a retention time or a period of time including the retention time, corresponding to the temporal location selected through the selector;
- identifies a segment which corresponds to the selected temporal location; reads out a compound name associated with the identified segment;
- shows the read compound name in a compound name display area;
- reads out mass spectrum data obtained at the selected point in time from each of data files stored in the compound information memory;
- creates a plurality of mass spectra based on the chromatographic mass spectrometry data acquired at the temporal location; and
- displays the created mass spectra vertically arranged in a mass spectra display area below the chromatogram display area, each of the mass spectra having a same scale on a mass axis and a same scale on an intensity axis as the other mass spectra and being arranged in a vertical direction,
- whereby the operator is able to check whether or not a peak at the temporal location on the chromatogram corresponds to an intended target compound to improve working efficiency and decrease incorrect operations.

10. The data-processing system for chromatographic mass spectrometry according to claim 9, wherein the display processor searches the compound information memory for a name of a compound also associated with the mass analysis condition under which the chromatographic mass spectrometry data for creating the chromatogram within the period of time is acquired.

11. The data-processing system for chromatographic mass spectrometry according to claim 9, wherein the plurality of mass spectra being further based on the chromatographic mass spectrometry data used for creating the chromatogram at the selected temporal location.

* * * * *